United States Patent
Breitenbach et al.

(10) Patent No.: US 6,171,583 B1
(45) Date of Patent: Jan. 9, 2001

(54) POWDERY IODINE COMPLEXES

(75) Inventors: Jörg Breitenbach, Mannheim; Axel Sanner, Frankenthal; Walter Denzinger, Speyer; Siegfried Lang, Ludwigshafen, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/068,305

(22) PCT Filed: Nov. 18, 1996

(86) PCT No.: PCT/EP96/05062

§ 371 Date: May 7, 1998

§ 102(e) Date: May 7, 1998

(87) PCT Pub. No.: WO97/19702

PCT Pub. Date: Jun. 5, 1997

(30) Foreign Application Priority Data

Nov. 29, 1995  (DE) ............................. 195 44 449

(51) Int. Cl.$^7$ .................................................. A61K 33/18
(52) U.S. Cl. ...................... 424/78.25; 424/78.22
(58) Field of Search ............... 424/78.37, 78.25

(56) References Cited

U.S. PATENT DOCUMENTS

| | | |
|---|---|---|
| 3,907,720 | 9/1975 | Field . |
| 3,992,562 | 11/1976 | Denzinger . |
| 5,152,987 | 10/1992 | Merianos . |

FOREIGN PATENT DOCUMENTS

| | | |
|---|---|---|
| 24 37 629 | 2/1976 | (DE) . |
| 44 14 254 | 10/1995 | (DE) . |
| 2 353 297 | 12/1977 | (FR) . |
| 1166766 | 10/1969 | (GB) . |
| 451717 | * 5/1973 | (SU) . |
| 92/04031 | 3/1992 | (WO) . |

OTHER PUBLICATIONS

Chem. Abst., vol. 99, No. 22, 1983, No. 176411 J. Macromol. Sci., Chem, A9(7), pp. 1085–1111 (1975).

* cited by examiner

*Primary Examiner*—Peter F. Kulkosky
(74) *Attorney, Agent, or Firm*—Keil & Weinkauf

(57) ABSTRACT

Complexes in powder form of iodine and a crosslinked polymer based on N-vinyl compounds are obtainable by dry heating of iodine and a polymer which is obtained by polymerization of monovinyl compounds (monomers A) whose vinyl group is bonded to a nitrogen atom of a nitrogen-containing heterocycle, in the presence of from 0.5 to 10% by weight, based on the monomers (A), of a compound (B) of the formula I;

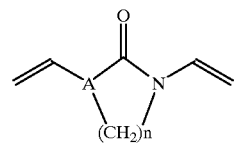

where A is —CH— or a nitrogen atom, and n is 2 or 3. The complexes are suitable for producing antidiarrheals.

2 Claims, No Drawings

POWDERY IODINE COMPLEXES

The present invention relates to complexes in powder form of iodine and a crosslinked polymer based on N-vinyl compounds, obtainable by dry heating of iodine and a polymer which is obtained by polymerization of monovinyl compounds (monomers A) whose vinyl group is bonded to a nitrogen atom of a nitrogen-containing heterocycle, in the presence of from 0.5 to 10% by weight, based on the monomers (A), of a compound (B) of the formula I;

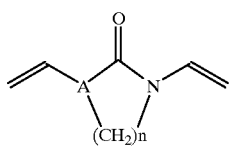

where A is —CH— or a nitrogen atom, and n is 2 or 3.

The invention furthermore relates to a process for preparing such complexes and to the use thereof for producing medicines for diarrhea.

It is known that crosslinked PVP, just like soluble PVP, forms complexes with iodine. The iodine is more firmly bound to the insoluble carrier than to the soluble one. Nevertheless, the amount of free iodine is sufficient in contact with moisture, eg. wound discharge and other body fluids, to kill microorganisms (cf., for example, WO 92/04031).

Processes for preparing crosslinked PVP-iodine are disclosed, for example, in U.S. Pat. No. 3,136,755 and U.S. Pat. No. 3,907,720. However, neither process leads to stable, uniform, free-flowing powders. Although U.S. Pat. No. 5,152,987 describes the preparation of a crosslinked PVP-iodine in the form of free-flowing powders, in this case isopropanol is used as solvent. This may lead to iodinated byproducts, quite apart from the medical, ecological and economic disadvantages of the use of organic solvents.

Although FR 2 353 297 describes the preparation of crosslinked PVP-iodine in the form of free-flowing powders by direct reaction of PVP and iodine, additional process steps are necessary, such as purification of the polymer by treatment with boiling water and ethanol and subsequent drying under reduced pressure, so that the process is not very suitable in practice.

It is an object of the present invention to provide complexes in the form of free-flowing powders of iodine and polymers based on N-vinyllactams which are obtainable in a straightforward manner.

We have found that this object is achieved by the iodine complexes defined at the outset, a process for the preparation and the use thereof.

Suitable monovinyl compounds (monomers A) are nitrogen heterocycles which are substituted on a ring nitrogen atom by a vinyl group, and suitable monomers (A) are, in particular, selected from the group consisting of N-vinyllactams, N-vinylimidazole and N-vinylcarbazole. Suitable N-vinyllactams are 5-, 6- or 7-membered lactams which may also have methyl, ethyl or propyl substituents on the ring. Preferred N-vinyllactams are N-vinylpyrrolidone and N-vinylcaprolactam.

The polymers used according to the invention can also be obtained from mixtures of the abovementioned monomers, for example by copolymerization of from 5 to 80% by weight of N-vinylpyrrolidone and from 20 to 95% by weight of N-vinylcaprolactam.

Further copolymers suitable according to the invention are also those which, besides the monomers (A), also comprise up to 80% by weight of other monoolefinically unsaturated monomers, especially vinyl esters such as vinyl acetate, vinyl propionate or vinyl butyrate, and acrylic acid and/or methacrylic acid and their $C_1$–$C_4$-alkyl esters.

Particularly preferred polymers comprise as monomers (A) N-vinylpyrrolidone or mixtures of N-vinylpyrrolidone and N-vinylcaprolactam.

The monomers (A) are polymerized in the presence of crosslinking compounds (B) of the general formula I. Particularly suitable compounds (B) are cyclic amides which have another vinyl group besides an N-vinyl group. Examples of suitable compounds are cyclic N,N'-divinylalkyleneureas such as N,N'-divinylethyleneurea or N,N'-divinylpropyleneurea. Also suitable furthermore are N,N'-divinyl-2-imidazolidone or N-vinyl-3-ethylidene-2-pyrrolidone or N-vinyl-3-ethylidene-2-piperidinone.

The polymers can be prepared by conventional processes, preferably by popcorn polymerization.

A suitable process is described, for example, in DE-C 20 59 484, in which case the polymerization takes place in aqueous medium in the presence of iron, an iron alloy which can be attacked by oxygen, or cobalt, zinc or tin.

Also suitable furthermore is the process described in DE-A 22 55 263, in which case the polymerization is started in aqueous solution by heating to 80° C. and completed at the boiling point of the water.

Likewise also suitable is the process, disclosed in DE-C 2437640, of polymerization with exclusion of oxygen in the presence of an α- or β-ketocarboxylic acid or of a corresponding methyl or ethyl ester.

The polymers can preferably be prepared by the process described in DE-C 24 37 629, in which case the polymerization is carried out with exclusion of oxygen in the presence of from 0.05 to 2% by weight of a sulfur compound with a valency of less than 6. Suitable sulfur compounds are selected from the group of sulfites, pyrosulfites, dithionites, sulfoxylates and sulfides, with the corresponding sodium salts preferably being employed.

The described processes can be carried out in the absence of conventional free-radical donors in aqueous solution.

The polymers employed according to the invention to prepare the complexes are essentially insoluble, ie. they comprise less than 2% by weight of soluble constituents. Preferred polymers have specific surface areas (BET) in the range 0.5–5 $m^2/g$, particularly preferably 0.7–4 $m^2/g$.

To prepare the iodine complexes according to the invention, the components, ie. the elemental iodine and the polymer, are vigorously mixed dry in the absence of a solvent and heated to from 50 to 150° C., preferably 70 to 120° C. The mixing and heating normally take place in a double cone mixer but can also be carried out in turbomixers, screw mixers or air-lift mixers. The duration of heating may depend, inter alia, on the size of the batch or on the required iodine content, and the skilled worker can establish this appropriately in a simple manner.

The freely available iodine content was determined in the examples below in the following manner.

Determination of the Available Iodine Content

About 2 g of insoluble iodine complex are suspended in 100 ml of distilled water in a 250 ml Erlenmeyer flask, acidified with glacial acetic acid and mixed with 25 ml of 0.1 N sodium thiosulfate solution. The mixture is then shaken for about 1 h until the suspension is completely decolorized. It is then filtered through a fluted filter, washed with about 50 ml of distilled water and titrated against 0.1 N iodine/potassium iodide solution with starch as indicator to a blue coloration.

Calculation $$\frac{(\text{ml of Na}_2\text{S}_2\text{O}_3 \text{ initially} - \text{iodine used}) \times 127}{\text{weight} \times 100} = \% \text{ available iodine}$$

Determination of the Partition Coefficient (PC)

1 g of a suspension of the insoluble iodine complex with 1% available iodine is vigorously shaken with 25 ml of n-heptane at 25° C. in a 50 ml graduated flask for 10 min. When phase separation has occurred after standing for about 2 minutes, the heptane phase is filtered off and its iodine content is determined by photometry. The iodine content of the aqueous phase is calculated from the difference between the iodine content employed and the iodine content in the heptane phase.

The iodine complexes obtainable according to the invention are stable on storage (no loss of iodine), uniform (no fluctuations in concentration) and free of byproducts for practical purposes, the powder is free-flowing, is not prone to caking on storage, has a specific surface area (BET) of from 0.5 $m^2/g$ to 5 $m^2/g$, preferably 0.9 to 4 $m^2/g$, and has an available iodine content of from 0.5 to 18, preferably 8 to 13, % by weight. They have the great advantage on use that, on the one hand, the iodine is so firmly bound that even oral administration is possible without complications in respect of the thyroid gland, but, on the other hand, sufficient iodine is released for reliable killing of pathogenic organisms (bacteria) and viruses. Oral use for diarrhea is thus part of the invention. The product acts in two ways: on the one hand it binds fluid while swelling and, on the other hand, it kills the pathogens.

EXAMPLES 1–11

In the following examples, the components were mixed in a double cone mixer.

Abbreviations used:

VP N-vinylpyrrolidone

VCAP N-vinylcaprolactam

The polymers used in the following examples were prepared as described in Example 1 of DE-A 2437629 and were adjusted to the required specific surface area (BET) (determined by the DIN 66131-132 method) by milling.

Polymer I:
insoluble PVP, BET=1.5–2 $m^2/g$
Polymer II:
insoluble PVP, BET=0.9 $m^2/g$ Polymer III:
insoluble PVP, BET=0.7–0.9 $m^2/g$
Polymer IV:
Polymer obtained by copolymerization of VP and VCAP in the ratio 1:5 by weight similar to Example 1 of DE-A 2437629, BET=1.3 $m^2/g$
Polymer V:
Polymer obtained by copolymerization of VP and VCAP in the ratio 1:1 by weight, BET=0.7 $m^2/g$ 1. 249 g of polymer I and 51 g of iodine were mixed at 70° C. for 2 h and at 100° C. for 24 h.
   Solids content: 97.7% by weight
   Available iodine content: 9.95% by weight
   Partition coefficient: 187
2. 451 g of polymer II and 85 g of iodine were mixed at 70° C. for 2 h and at 100° C. for 24 h.
   Solids content: 96.9% by weight
   Available iodine content: 9.32% by weight
   Partition coefficient: 220
3. 60 kg of polymer III and 12.3 kg of iodine were mixed at room temperature for 1 h, at 70° C. for 2 h and at 100° C. for 20 h.
   Solids content: 97.0% by weight
   Available iodine content: 12.0% by weight
   Partition coefficient: 173
4. 200 g of polymer III and 41 g of iodine were mixed at room temperature for 1 h, at 70° C. for 2 h and at 100° C. for 10 h.
   Solids content: 97.5% by weight
   Available iodine content: 10.3% by weight
   Partition coefficient: 293
5. 451 g of polymer IV and 85 g of iodine were mixed at 70° C. for 2 h and at 100° C. for 24 h.
   Solids content: 94.96% by weight
   Available iodine content: 7.4% by weight
   Partition coefficient: 779
6. 451 g of polymer V and 85 g of iodine were mixed at 70° C. for 2 h and at 100° C. for 24 h.
   Solids content: 91.5% by weight
   Available iodine content: 10.9% by weight
   Partition coefficient: 249.8
7. 451 g of polymer V and 85 g of iodine were mixed at 70° C. for 2 h and at 120° C. for 16 h.
   Solids content: 90.5% by weight
   Available iodine content: 10.5% by weight
   Partition coefficient: 200.8
8. 300 kg of polymer II and 60 kg of iodine were mixed at room temperature for 1 h, at 70° C. for 2 h and at 95° C. for 30 h.
   Solids content: 97.1% by weight
   Available iodine content: 11.02% by weight
   Partition coefficient: 220
9. 60 kg of polymer III and 12.3 kg of iodine were mixed at room temperature for 1 h, at 70° C. for 2 h and at 105° C. for 10 h.
   Solids content: 97.0% by weight
   Available iodine content: 11.6% by weight
   Partition coefficient: 171
10. 60 kg of polymer III and 12.3 kg of iodine were mixed at room temperature for 1 h, at 70° C. for 2 h and at 105° C. for 20 h.
    Solids content: 97.0% by weight
    Available iodine content: 11.3% by weight
    Partition coefficient: 311
11. 60 kg of polymer III and 12.3 kg of iodine were mixed at room temperature for 1 h, at 70° C. for 2 h and at 115° C. for 20 h.
    Solids content: 97.0% by weight
    Available iodine content: 13.3% by weight
    Partition coefficient: 290

Formulation of Antidiarrheals

EXAMPLE 12

| | |
|---|---|
| Complex of Example 1 | 50 mg |
| Microcrystalline cellulose | 5 mg |
| Magnesium stearate | 0.5 mg |

EXAMPLE 13

| | |
|---|---|
| Complex of Example 2 | 200 mg |
| Insoluble PVP | 1800 mg |
| Microcrystalline cellulose | 100 mg |
| Silica | 100 mg |
| Magnesium stearate | 10 mg |

The formulations of Examples 12 and 13 are suitable for direct tabletting.

EXAMPLE 14

A mixture of 200 mg of a complex from Example 2 and 1800 mg of insoluble PVP was subjected with 20 mg of povidone K 90 and 9.1 g of ethanol to a wet granulation. After the granules had been dried, 10 mg of magnesium stearate were added. The formulation can be tabletted under conventional conditions.

We claim:

1. A storage stable complex in free-flowing powder form of iodine and a crosslinked polymer based on N-vinyl compounds, obtainable by dry heating of iodine and a polymer which is obtained by polymerization of monovinyl compounds (monomers A) whose vinyl group is bonded to a nitrogen atom of a nitrogen-containing heterocycle which is a member selected from the group consisting of N-vinylimidazole, N-vinyl carbazole, N-vinyl-pyrrolidone, and N-vinylcaprolactam and mixtures thereof, and optionally, up to 80% by weight of monoolefinically unsaturated co-monomer selected from the group consisting of vinyl acetate, vinyl propionate and vinyl butyrate, and acrylic acid and/or methacrylic acid and their C1–C4-alkyl esters in the presence of from 0.5 to 10% by weight, based on the monomers (A), of a compound (B) of the formula I;

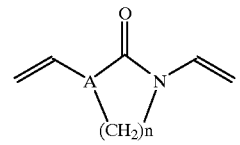

where A is —CH— or a nitrogen atom, and n is 2 or 3.

2. A method of treating diarrhea which comprises administering to a patient in need thereof an effective amount of the complex defined in claim 1.

* * * * *

UNITED STATES PATENT AND TRADEMARK OFFICE
CERTIFICATE OF CORRECTION

PATENT NO. : 6,171,583
DATED : January 9, 2001
INVENTOR(S) : Breitenbach et al.

It is certified that error appears in the above-identified patent and that said Letters Patent is hereby corrected as shown below:

Col. 6, claim 1, line 8, "Cl-C4-alkyl" should be --C1-C4-alkyl--.

Signed and Sealed this

Twenty-ninth Day of May, 2001

Attest:

NICHOLAS P. GODICI

Attesting Officer      Acting Director of the United States Patent and Trademark Office

UNITED STATES PATENT AND TRADEMARK OFFICE
CERTIFICATE OF CORRECTION

PATENT NO.     : 6,171,583 B1
DATED          : January 9, 2001
INVENTOR(S)    : Breitenbach et al.

It is certified that error appears in the above-identified patent and that said Letters Patent is hereby corrected as shown below:

Column 6, claim 1,
Line 8, "C1-C4-alkyl" should be -- $C_1$-$C_4$-alkyl --.

This certificate supersedes Certificate of Correction issued May 29, 2001.

Signed and Sealed this

Tenth Day of December, 2002

JAMES E. ROGAN
*Director of the United States Patent and Trademark Office*